US007933377B2

(12) United States Patent
Hsieh et al.

(10) Patent No.: US 7,933,377 B2
(45) Date of Patent: Apr. 26, 2011

(54) METHOD OF CT PERFUSION IMAGING AND APPARATUS FOR IMPLEMENTING SAME

(75) Inventors: Jiang Hsieh, Brookfield, WI (US); Paul E. Licato, Wauwatosa, WI (US); Akira Hagiwara, Hino (JP); Mark Vincent Profio, Elm Grove, WI (US); Karen Ann Procknow, Willowbrook, IL (US); Saad Ahmed Sirohey, Pewaukee, WI (US); Srinivas Aluri, Pewaukee, WI (US); Olga Imas, Mequon, WI (US)

(73) Assignee: General Electric Company, Schenectady, NY (US)

( * ) Notice: Subject to any disclaimer, the term of this patent is extended or adjusted under 35 U.S.C. 154(b) by 13 days.

(21) Appl. No.: 12/477,677

(22) Filed: Jun. 3, 2009

(65) Prior Publication Data

US 2010/0310040 A1     Dec. 9, 2010

(51) Int. Cl.
*A61B 6/00* (2006.01)
(52) U.S. Cl. .................................. 378/8; 378/4; 378/15
(58) Field of Classification Search .................... 378/4, 8
See application file for complete search history.

(56) References Cited

U.S. PATENT DOCUMENTS

| | | | | |
|---|---|---|---|---|
| 4,789,929 | A * | 12/1988 | Nishimura et al. | 378/15 |
| 5,396,418 | A * | 3/1995 | Heuscher | 378/15 |
| 6,504,892 | B1 * | 1/2003 | Ning | 378/4 |
| 2004/0008819 | A1 * | 1/2004 | Drummond et al. | 378/162 |
| 2004/0101085 | A1 * | 5/2004 | Edic | 378/4 |
| 2005/0074085 | A1 * | 4/2005 | Hsieh et al. | 378/4 |
| 2006/0133564 | A1 * | 6/2006 | Langan et al. | 378/8 |
| 2006/0140336 | A1 * | 6/2006 | Russinger et al. | 378/4 |
| 2007/0071160 | A1 * | 3/2007 | Nishide et al. | 378/4 |
| 2007/0217567 | A1 * | 9/2007 | Noshi et al. | 378/4 |
| 2007/0258558 | A1 * | 11/2007 | Nishide et al. | 378/8 |
| 2009/0022268 | A1 * | 1/2009 | Kudo | 378/15 |

OTHER PUBLICATIONS

Licato et al., "Investigation of the Effects of Sampling Interval on Parameter Estimates from CT Perfusion," Radiological Society of North America, Inc., 2006.
Licato et al., Presentation—"Investigation of the Effects of Sampling Interval on Parameter Estimates from CT Perfusion," Radiological Society of North America, Inc., 2006.

* cited by examiner

*Primary Examiner* — Edward J Glick
*Assistant Examiner* — Alexander H Taningco
(74) *Attorney, Agent, or Firm* — Ziolkowski Patent Solutions Group, SC

(57) ABSTRACT

A CT system includes a scintillator array having a first length in an axial direction of the CT system, the scintillator array includes a plurality of scintillator cells along the first length. The CT system includes a controller configured to repeatedly position a subject fore and aft along the axial direction and over a second length of the CT system, the second length greater than the first length, energize an x-ray source to emit x-rays toward the subject while the subject is being repeatedly positioned, and obtain non-uniform projection data of the subject from the scintillator array, the non-uniform projection data comprising the x-rays received from the x-ray source while the subject is repeatedly positioned. The CT system includes a computer programmed to reconstruct a plurality of temporally non-uniformly spaced images from the non-uniform projection data, interpolate the plurality of non-uniform images to form a plurality of temporally uniform images, and apply a perfusion map generation process to the plurality of temporally uniform images.

22 Claims, 6 Drawing Sheets

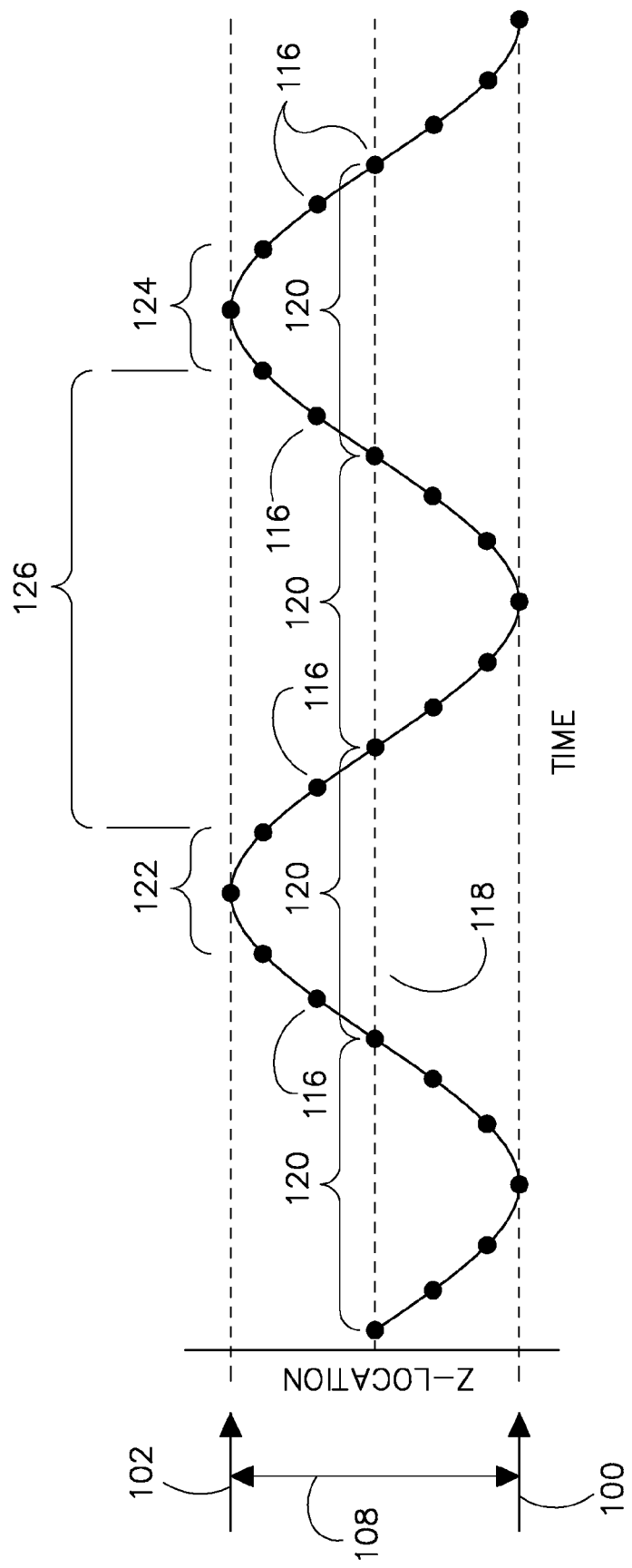

METHOD OF CT PERFUSION IMAGING AND APPARATUS FOR IMPLEMENTING SAME

BACKGROUND OF THE INVENTION

The invention relates generally to diagnostic imaging and, more particularly, to a method of CT perfusion imaging and an apparatus for implementing same.

Typically, in computed tomography (CT) imaging systems or scanners, an x-ray source emits a fan-shaped beam toward a subject or object, such as a patient. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point that may be stationary or wobbled with respect to the rotating target during x-ray emission. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. The outputs of the photodiodes are then transmitted to the data processing system for image reconstruction. Typically, the scintillator is part of an array of scintillators.

The scintillator array typically extends in both circumferential (X) and axial (Z) directions of the CT scanner as is understood in the art. In a perfusion application, the axial coverage of the detector traditionally defines the axial region that may be studied. Thus for a 4 cm detector, as an example, a perfusion study may be conducted having a 4 cm organ positioned such that the source and detector rotate about the organ in a single axial location. However, for organs having greater than 4 cm in axial length (12-16 cm of coverage is desired for head perfusion studies, and 16 cm or more of coverage is desired for a liver perfusion study, as examples), the information obtained will be limited and important diagnostic imaging information may be missed. Coverage may be increased by using consecutive series of scans at contiguous axial locations, each with its own contrast injection. However, this tends to correspondingly increase both the contrast load and the radiation dose to the patient.

To reduce both the contrast load and radiation dose while increasing anatomical coverage, axial coverage of the detector may be increased by increasing the overall z-length of the array. However, because desired coverage may be 16 cm or more, this tends to increase the cost of the detector, hence the overall system, to prohibitive levels.

Alternatively, a subject may be positioned and data may be obtained during a single bolus injection at two axial locations in a volume axial shuttle (VAS) mode, or over an extended region in a volume helical shuttle (VHS). In VHS, while the table moves fore and aft, helical scanning data may be obtained throughout the range of motion and contrast uptake information and dynamic information can be obtained over time. During VHS the table may travel from a first Z location to a second Z location and dwell or idle at each first and second Z location while obtaining projection data throughout. Data thus acquired at a center of subject positions between first and second Z locations will be obtained at a generally uniform time interval as the table sweeps fore and aft. However, data obtained off-center will be non-uniform in time due to the shuttle motion of the table, with the most extreme non-uniformity occurring at the extremes of table motion.

In other words, data may be repeatedly sampled at the first Z location during dwell or idle of the table. The table then moves to the second Z location and dwells there, during which time data is repeatedly sampled at the second Z location. This results in a plurality of scans being obtained at the first Z location, and a gap in first Z location data then occurs while the table moves to the second Z location, dwells there and obtains projection data, and moves back to the first Z location. Likewise, a plurality of scans are obtained at the second Z location, and a gap in second Z location data then occurs while the table moves to the first Z location, dwells there, and moves back. The presence of these gaps, or sampling intervals, results in a non-uniform set of data that determines the accuracy of the perfusion map. To produce an acceptable perfusion map, the sampling interval needs to be less than approximately 3.2 seconds. This limitation of approximately 3.2 seconds thus limits the overall coverage in Z of VHS and limits the amount of stationary samples that may be taken during dwell or idle. Accordingly, if it is desired to conduct a perfusion study of an organ that is greater in z-length than can be obtained with a time limitation between first and second locations, then an additional perfusion study may be conducted—but at the expense of increased contrast load and radiation dose to the patient.

Therefore, it would be desirable to design an apparatus and method of VHS perfusion imaging having an increased ability to obtain perfusion data of a large organ without having to include multiple contrast injections.

BRIEF DESCRIPTION OF THE INVENTION

The invention is a directed method and apparatus for CT perfusion.

According to one aspect, a CT system includes a scintillator array having a first length in an axial direction of the CT system, the scintillator array includes a plurality of scintillator cells along the first length. The CT system includes a controller configured to repeatedly position a subject fore and aft along the axial direction and over a second length of the CT system, the second length greater than the first length, energize an x-ray source to emit x-rays toward the subject while the subject is being repeatedly positioned, and obtain non-uniform projection data of the subject from the scintillator array, the non-uniform projection data comprising the x-rays received from the x-ray source while the subject is repeatedly positioned. The CT system includes a computer programmed to reconstruct a plurality of temporally non-uniformly spaced images from the non-uniform projection data, interpolate the plurality of non-uniform images to form a plurality of temporally uniform images, and apply a perfusion map generation process to the plurality of temporally uniform images.

According to another aspect, a method of perfusion map generation includes transporting a patient table fore and aft along an axial dimension of a CT system to cover a z-length of a subject that is larger than a z-length of a CT detector of the CT system, acquiring projection data over the z-length of the subject, and generating a plurality of temporally non-uniformly spaced subject images using the projection data. The method further includes applying an interpolation process to the plurality of temporally non-uniformly spaced subject images to form a plurality of interpolated images, and applying a perfusion map generation process to the plurality of interpolated images to produce a final perfusion map.

According to yet another aspect, a computer readable storage medium having thereon a computer program thereon is configured to obtain volume helical shuttle (VHS) data of a subject over a range of CT table motion, the range of CT table motion greater than a coverage of a CT detector, generate a plurality of images using the VHS data, and interpolate the plurality of images to form a uniform grid having a finer temporal sampling increment than the obtained VHS data. The computer program is further configured to apply a perfusion map generation process to the uniform grid, and present the perfusion map to a user.

Various other features and advantages will be made apparent from the following detailed description and the drawings.

BRIEF DESCRIPTION OF THE DRAWINGS

The drawings illustrate one preferred embodiment presently contemplated for carrying out the invention.

In the drawings:

FIG. 7 is an illustration of projection data acquired at a plurality of z-locations of motion, as a function of time, according to an embodiment of the invention.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
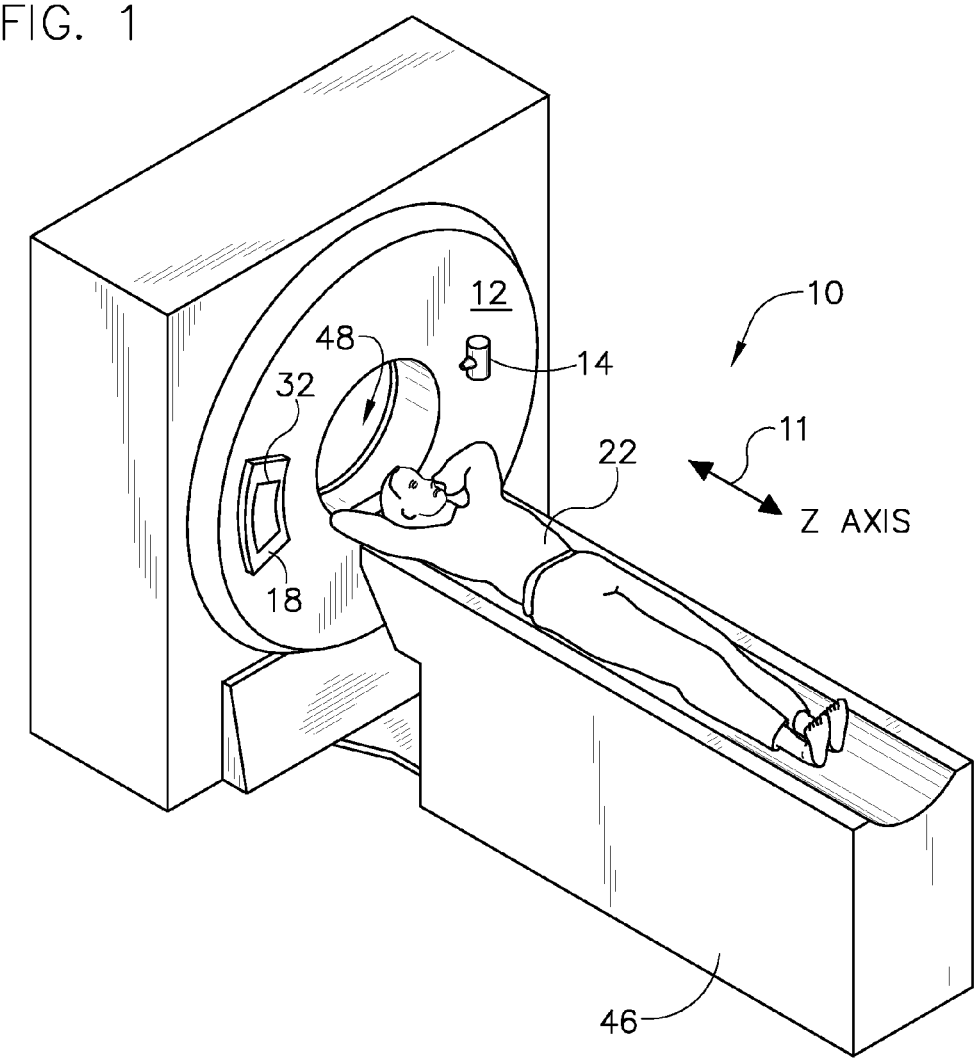
FIG. 1 is a pictorial view of a CT imaging system.
Figure 2:
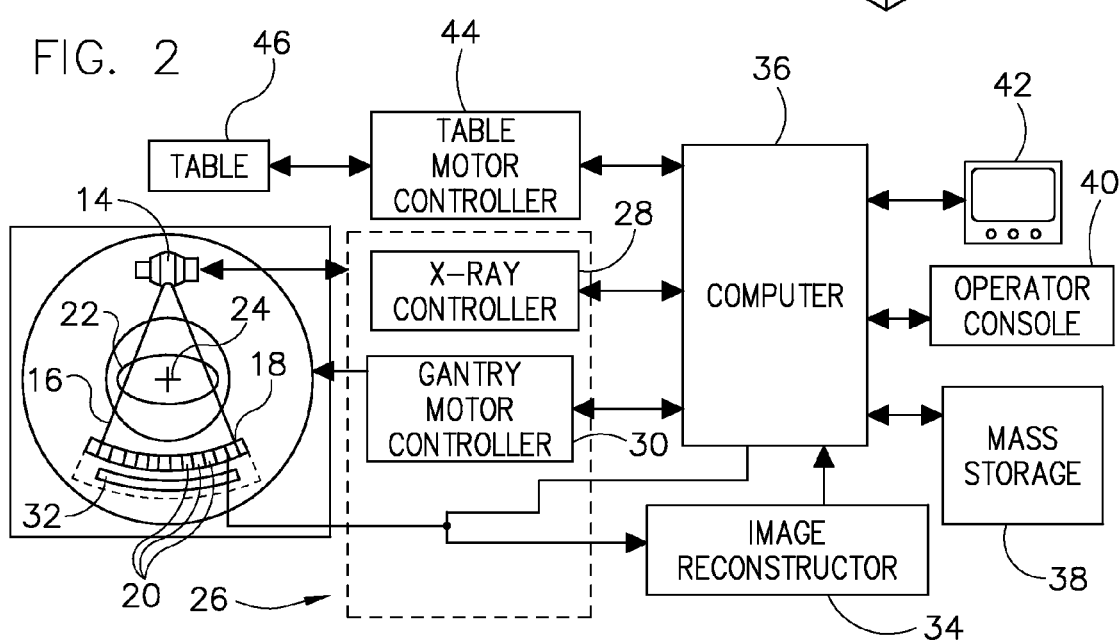
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Gantry 12 includes a motorized table 46 to position a medical patient or subject 22 along a patient or z-axis 11 of imaging system 10. Referring now to FIG. 2, detector assembly 18 is formed by a plurality of detectors 20 and data acquisition systems (DAS) 32. The plurality of detectors 20 sense the projected x-rays 16 that pass through the subject 22, and DAS 32 converts the data to digital signals for subsequent processing. Each detector 20 produces an analog electrical signal that represents the intensity of an impinging x-ray beam and hence the attenuated beam as it passes through the subject 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls the motorized table 46 to position subject 22 and gantry 12. Particularly, table 46 moves subject 22 along z-axis 11 through a gantry opening 48 of FIG. 1 in whole or in part.

Figure 3:
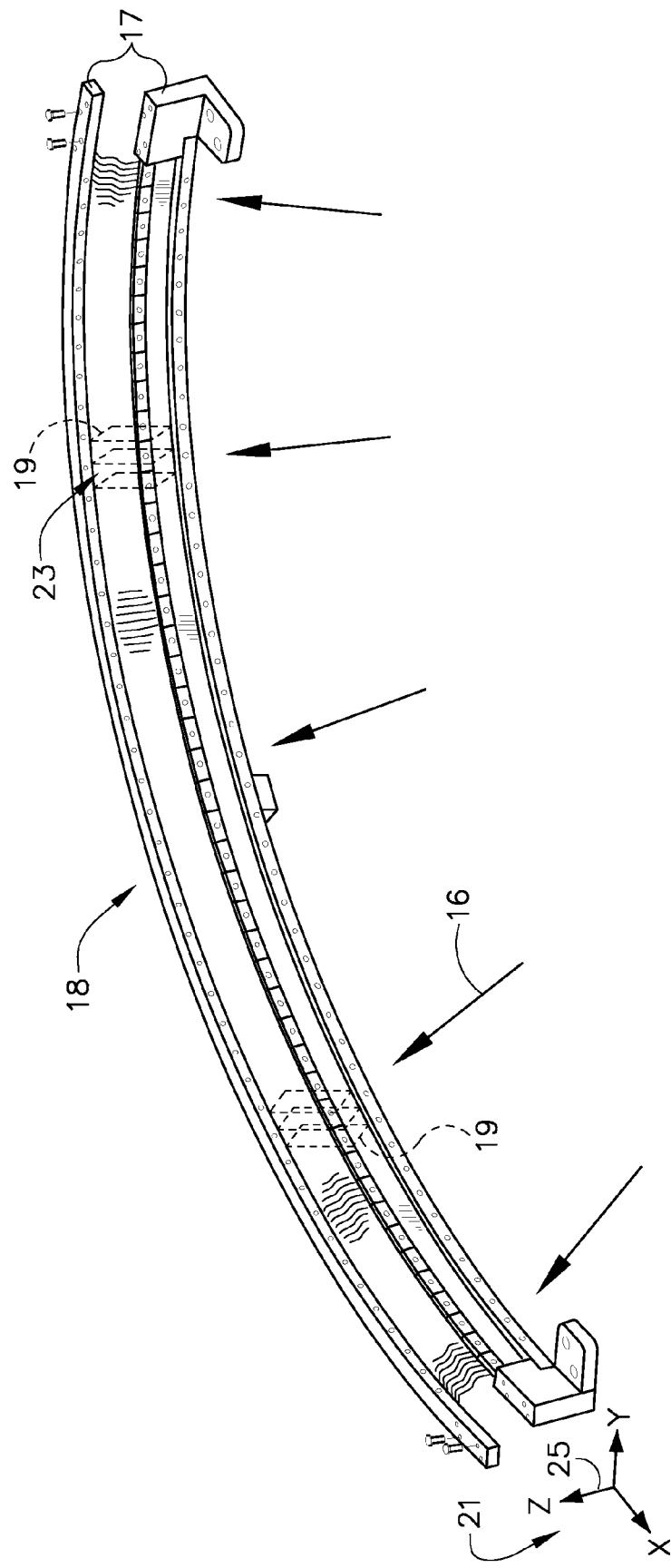
FIG. 3 is a perspective view of one embodiment of a CT system detector array.

As shown in FIG. 3, detector assembly 18 positioned within coordinate system 21 includes rails 17 having collimating blades or plates 19 placed therebetween. As illustrated, collimating plates 19 are positioned to form gaps 23 therebetween along an X-direction of detector assembly 18, the plates extending in an axial, slice or z-direction 25 as defined by coordinate system 21. Z-direction 25 of FIG. 3 corresponds to z-axis 11 of FIG. 1. Plates 19 are positioned to collimate x-rays 16 through gaps 23 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
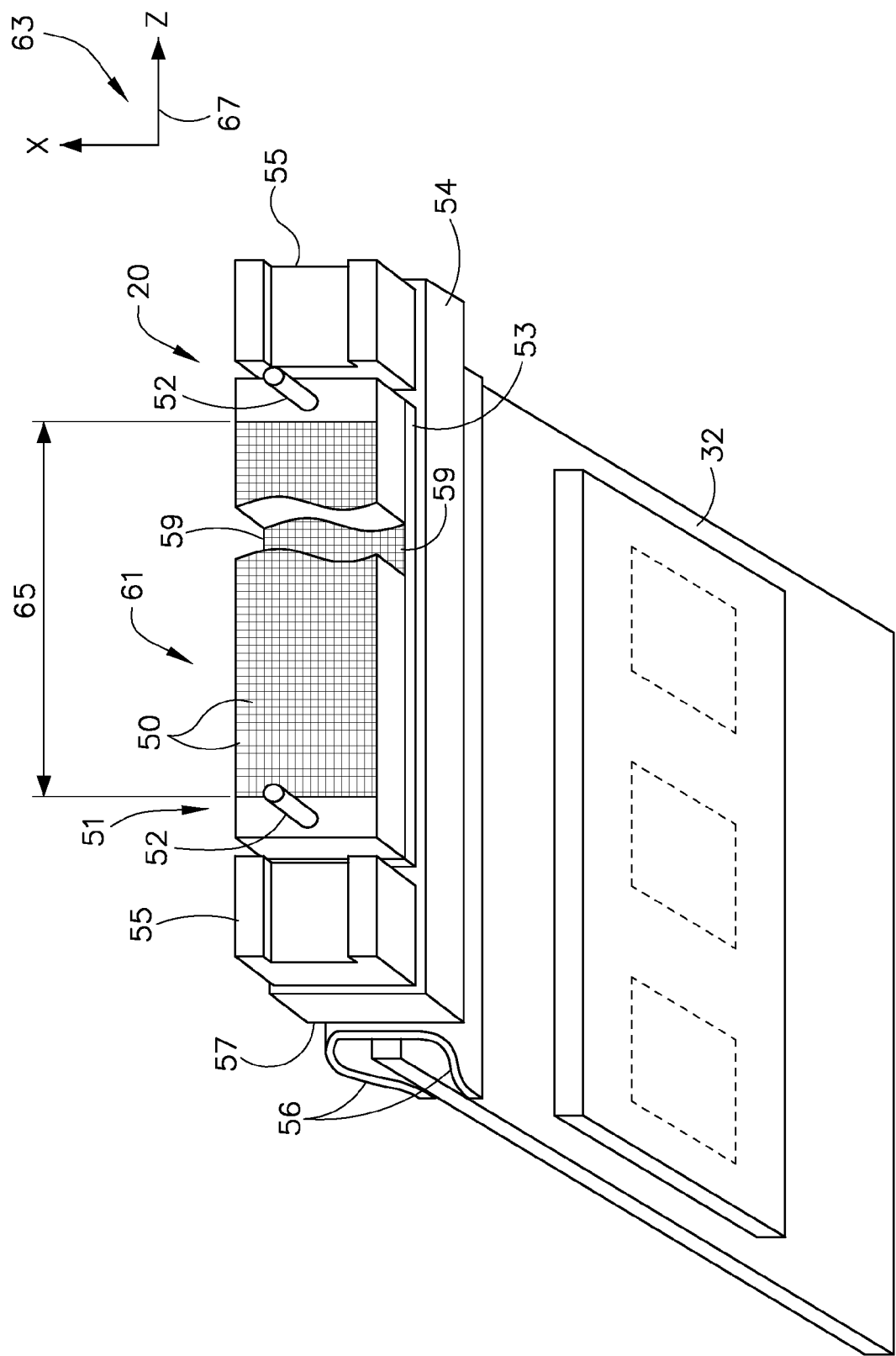
FIG. 4 is a perspective view of one embodiment of a detector.

Referring to FIG. 4, detector 20 includes DAS 32, with each detector 20 including a number of detector elements 50 arranged in pack 51 in an array of 64×16 scintillating crystals 61. In the illustrated embodiment, the array of pixels 61 extends in both X and Z directions of detector 20, as defined by coordinate system 63. The z-axis (or slice axis), particularly, is illustrated as element 67 in coordinate system 63. The array of crystals 61 includes a z-length or amount of z-coverage 65. Z-length 65 and z-axis 67 correspond to z-direction 25 of coordinate system 21 of FIG. 3, and also correspond to z-axis 11 of FIG. 1.

Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
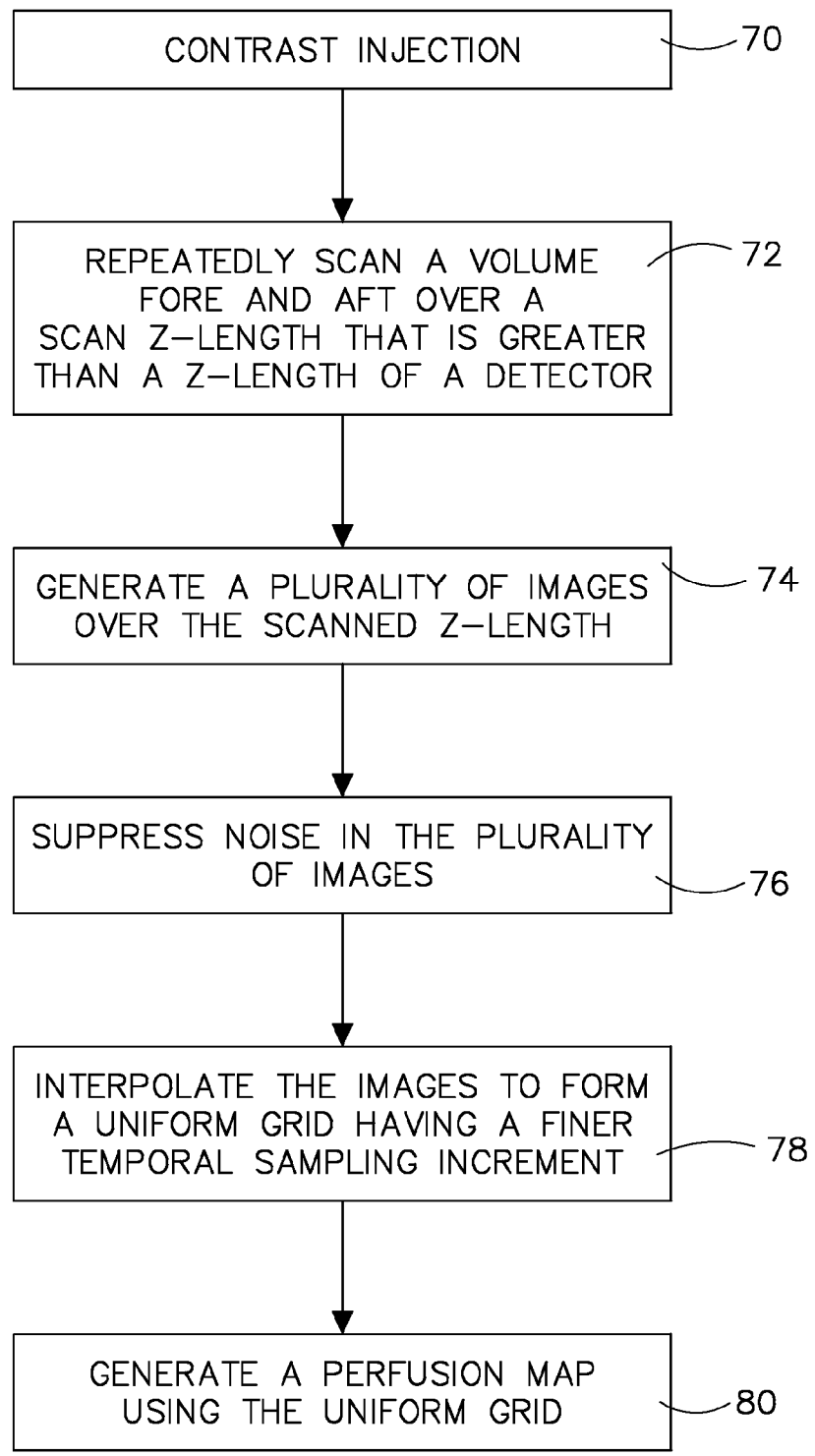
FIG. 5 is a process for generating a perfusion map according to the invention.

Imaging system 10 may be used to acquire projection data and generate a perfusion map according to the invention and as illustrated in process or flowchart 68 of FIG. 5. Process 68 begins by administration of a contrast agent, such as iodine, at step 70. As the contrast agent passes through a volume or region of interest (ROI), at step 72 the ROI is repeatedly scanned fore and aft over a scan z-length that is greater than a z-length of a detector.

Figure 6:
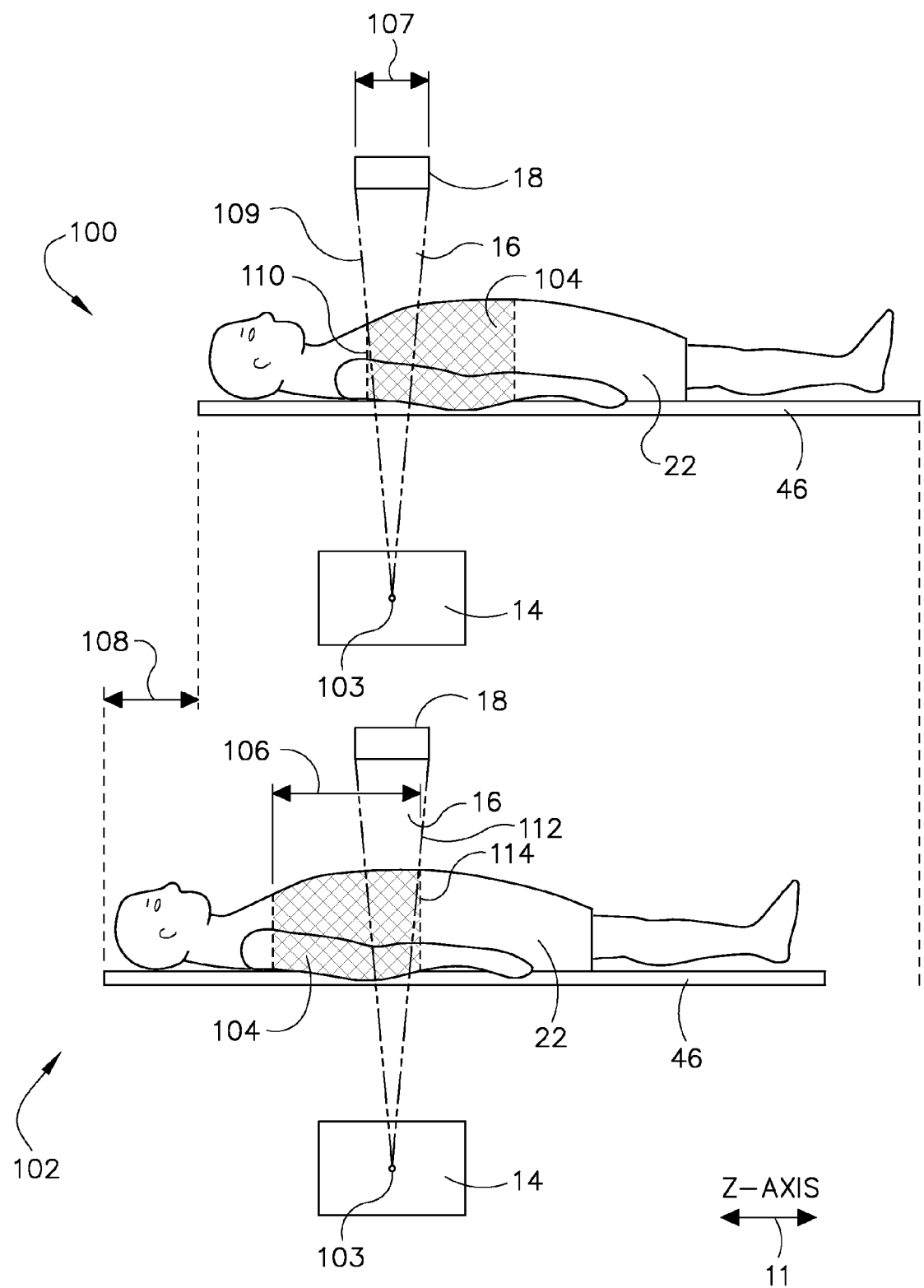
FIG. 6 is a subject shown at first and second positions with respect to a source and detector, for projection data acquisition.

As an illustration, referring now to FIG. 6, subject 22 is positioned on motorized table 46, as also illustrated in imaging system 10 of FIGS. 1 and 2. Subject 22 is first positioned at a first location 100 and moved to a second location 102 along z-axis 11 and with respect to x-ray source 14 and detector assembly 18. X-rays 16 are caused to emit from a focal spot 103 of x-ray source 14 that is, as an example, x-ray source 14 of imaging system 10, and x-rays 16 are emitted toward detector assembly 18 thereof.

Subject 22 includes an ROI 104 having a z-length 106 that may include a liver in the subject's torso as illustrated, according to an embodiment of the invention. According to other embodiments, ROI 104 may include a head or other region of interest on which a perfusion study may be conducted. Projection data is acquired by detector assembly 18 having a z-length 107 and while imaging table 46 is caused to move fore and aft through a range 108 of z-motion between first location 100 and second location 102 that is greater than z-length 107 of detector assembly 18. Projection data is acquired at a plurality of locations during the table motion, and the data acquired may be helically scanned according to embodiments of the invention.

Z-length 106 and range 108 of z-motion are illustrated as having different lengths due to the finite z-length of detector assembly 18 and the acquisition of projection data at the extremes of detector assembly 18. In other words, first location 100 illustrates a first edge 109 of x-rays 16 coincident with an edge 110 of ROI 104. Likewise, second location 102 illustrates a second edge 112 of x-rays 16 coincident with an edge 114 of ROI 104. Thus, in order to obtain projection data over an entire z-length of 106 of ROI 104, it is evident that range 108 of table motion need not match z-length 106 of ROI 104. However, one skilled in the art will recognize that additional projection data may be obtained of ROI 104 by extending range 108 to be, for instance, equal to z-length 106 of ROI 104, as an example.

As one skilled in the art will recognize, for continuous motion fore and aft the plurality of locations 104 where projection data is acquired may follow a sinusoidal curve while projection data is acquired at discrete locations of the table motion over range 108. Thus, referring to FIG. 7, as imaging table 46 illustrated in FIG. 6 moves continuously fore and aft over range 108 between first position 100 and second position 102, projection data is acquired at generally sinusoidally distributed locations 116 according to embodiments of the invention. However, one skilled in the art will recognize that imaging table 46 may be caused to dwell at first and second positions 100, 102 and that the motion of imaging table 46 may be non-sinusoidal as a function of time. For instance, projection data may be acquired at first location 100 while dwelling there and not continuously moving, then imaging table 46 may be caused to move to second location 102 and dwell there while projection data is acquired at second location 102. As such, projection data may be acquired over a z-length of the ROI with any periodic or non-periodic motion of table 46 according to embodiments of the invention. The process may be periodically or non-periodically repeated, and data may be acquired having durations of time of 3.2 seconds or more before the table returns again to first location 100.

For periodic or sinusoidal motion of table 46 and because of the fore and aft motion of imaging table 46, projection data acquired at a midpoint 118 as table 46 moves along range 108 is generally uniformly spaced in time as illustrated at 120. However, data acquired at extremes of motion 100, 102 of table 46 will generally be spaced non-uniformly in time. Thus, as an example, data 122 may be acquired with table 46 positioned at second location 102, and data 124 may later be acquired (again at second location 102) having a gap 126 therebetween. Gap 126 between data 122 and 124 is thus non-uniformly obtained in time, causing non-uniformly distributed projection data to be acquired during a perfusion study. The non-uniformity of data is exacerbated by increased idling or dwelling at first and second locations 100, 102 and by increasing range 108. Such non-uniformly acquired projection data may be corrected according to embodiments of the invention.

Thus, referring back to FIG. 5, non-uniformly distributed projection data may be obtained at step 72 by repeatedly scanning a volume or ROI fore and aft over a scanning z-length that is greater than a z-length of a detector. At step 74, a plurality of images is generated or reconstructed over the scanned z-length and using techniques as commonly known in the art. At step 76, noise may be suppressed in the plurality of images according to the invention.

Noise suppression of step 76 may be accomplished via a number of noise reduction algorithms. According to one embodiment, noise suppression is accomplished by adaptive filtering of projections followed by a filtered back-projection operation. According to another embodiment, noise suppression is accomplished by adaptive post-processing on filtered back-projection generated images. According to yet another embodiment of the invention, noise suppression is accomplished by iterative reconstruction.

As an example, an anisotropic diffusion process may be used to suppress noise as described in the following equation:

$$\frac{\partial I(x, y, t)}{\partial t} = div[d(\|\nabla I\| \cdot \nabla I)]; \qquad \text{Eqn. 1}$$

where an intensity of pixel I(x,y) is updated based on a gradient of its value with its neighbor pixels, and d is a positive decreasing diffusion function.

Referring still to process 68, the plurality of images is interpolated at step 78 to form a uniform grid having a finer temporal sampling increment. Thus, the reconstructed images undergo a high-order interpolation process as described by the following equation:

$$f'(x, y, z) = \sum_{k=-N}^{N} w(k) f(x, y, z+k); \qquad \text{Eqn. 2}$$

where $f'(x,y,z)$ is the interpolated images, $f(x,y,z)$ denotes the originally reconstructed images, $w(k)$ is an interpolation coefficient or function, and N is a parameter that determines a size of the interpolation. The interpolation function $w(k)$ is selected such that high-frequency information is maintained. One such function that exhibits such property, according to an embodiment of the invention, is a Lagrange interpolator as described by the following equation:

$$w(x_j) = \prod_{k=1, k \neq j}^{n} \frac{x - x_k}{x_j - x_k}. \qquad \text{Eqn. 3}$$

As such, because step 78 results in uniformly gridded data, a traditional or conventional perfusion map generation process may then be generated at step 80, as is commonly understood in the art, the results of which may be presented to a user for diagnosis. Accordingly, non-uniformly spaced perfusion data may be obtained, noise suppressed, and uniformly interpolated and corrected according to embodiments of the invention.

Since tomographic reconstruction is a linear process, the interpolation process carried out in the image space can be applied in the projection space. That is, the projection, $p(\gamma, \beta, z)$, is weighted prior to the filtered back projection process, where $\gamma$ is the fan angle, $\beta$ is the projection angle, and $z$ is the detector row:

$$p'(\gamma, \beta, z) = \alpha(\gamma, \beta, z) \times p(\gamma, \beta, z) \quad \text{Eqn. 4}$$

where $\alpha(\gamma, \beta, z)$ is a weighting function. In the backprojection process, instead of backprojecting over a view range sufficient for a single reconstruction (e.g., 360°), the new process generates backprojections over a much larger view range. The new view range is determined by the temporal-extent of the original images used for the image-space interpolation. For example, if Eqn. 2 uses four neighboring slices to produce a final image, and the very first view used to produce the first of the four neighboring slice is v1, and the last view used to produce the last of the four neighboring slices is v2, the reconstruction is then carried out over v1 to v2. For computational efficiency, however, some of the projections located between v1 and v2 that do not contribute to the current slice location can be ignored.

In the described embodiment, the x-ray tube is assumed to be continuously "on" during the entire VHS acquisition process. However, the x-ray tube can be turned off briefly during the period of time in which the table does not move as fast or dwells to reduce dose to patient. For example, near both ends of the VHS scan range (such as first and second Z locations 100, 102 as illustrated in FIG. 6), the table speed dwells or reaches near zero to allow reversing the table traveling direction. The temporal samples near these regions are more frequent than the middle of the z-range. Because multiple images can be generated for the same z-location with little difference temporally, redundant sampling pattern does not provide significant new information and only significantly contributes to the patient dose. Thus, the x-ray tube can be temporarily turned off in these regions.

Since most organs-of-interests are not shaped like a cylinder (with an axis parallel to the z-axis), the gantry can be tilted forward and backward continuously in sync with the table fore and aft motion during VHS data acquisition to correspond with a shape of an organ-of-interest. This approach can potentially reduce the table traveling distance and, therefore, reduce the round-trip time to improve the perfusion map accuracy. In addition, since the gantry angle changes constantly at both ends of the VHS scan range, redundant sampling is avoided since the orientation of the projection plane changes constantly.

In the previous discussion, the gantry speed is assumed to be constant. In another embodiment, however, the gantry speed can be changed dynamically during the scan. For example, when the patient table approaches both ends of the acquisition range, the gantry speed is reduced to account for the dwell or slow table location change. In a preferred embodiment, the gantry speed can be designed to be substantially proportional to the patient table traveling speed. In such design, the temporal spacing of the reconstructed images becomes substantially uniform in time. This approach can be used to reduce or eliminate the needs for interpolation.

A technical contribution for the disclosed method and apparatus is that it provides for a computer implemented method of VHS perfusion imaging having an increased ability to obtain perfusion data of a large organ without having to include multiple contrast injections.

According to one embodiment, a CT system includes a scintillator array having a first length in an axial direction of the CT system, the scintillator array includes a plurality of scintillator cells along the first length. The CT system includes a controller configured to repeatedly position a subject fore and aft along the axial direction and over a second length of the CT system, the second length greater than the first length, energize an x-ray source to emit x-rays toward the subject while the subject is being repeatedly positioned, and obtain non-uniform projection data of the subject from the scintillator array, the non-uniform projection data comprising the x-rays received from the x-ray source while the subject is repeatedly positioned. The CT system includes a computer programmed to reconstruct a plurality of temporally non-uniformly spaced images from the non-uniform projection data, interpolate the plurality of non-uniform images to form a plurality of temporally uniform images, and apply a perfusion map generation process to the plurality of temporally uniform images.

According to another embodiment, a method of perfusion map generation includes transporting a patient table fore and aft along an axial dimension of a CT system to cover a z-length of a subject that is larger than a z-length of a CT detector of the CT system, acquiring projection data over the z-length of the subject, and generating a plurality of temporally non-uniformly spaced subject images using the projection data. The method further includes applying an interpolation process to the plurality of temporally non-uniformly spaced subject images to form a plurality of interpolated images, and applying a perfusion map generation process to the plurality of interpolated images to produce a final perfusion map.

According to yet another embodiment, a computer readable storage medium having thereon a computer program thereon is configured to obtain volume helical shuttle (VHS) data of a subject over a range of CT table motion, the range of CT table motion greater than a coverage of a CT detector, generate a plurality of images using the VHS data, and interpolate the plurality of images to form a uniform grid having a finer temporal sampling increment than the obtained VHS data. The computer program is further configured to apply a perfusion map generation process to the uniform grid, and present the perfusion map to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
a scintillator array having a first length in an axial direction of the CT system, the scintillator array comprising a plurality of scintillator cells along the first length;
a controller configured to:
repeatedly position a subject fore and aft along the axial direction and over a second length of the CT system, the second length greater than the first length;
energize an x-ray source to emit x-rays toward the subject while the subject is being repeatedly positioned; and
obtain non-uniform projection data of the subject from the scintillator array, the non-uniform projection data comprising the x-rays received from the x-ray source while the subject is repeatedly positioned; and a computer programmed to:
reconstruct a plurality of temporally non-uniformly spaced images from the non-uniform projection data;
interpolate the plurality of non-uniform images to form a plurality of temporally uniform images; and
apply a perfusion map generation process to the plurality of temporally uniform images.

2. The CT system of claim 1 wherein the computer is programmed to tilt a gantry of the CT system to correspond with a shape of an organ-of-interest.

3. The CT system of claim 1 wherein the computer is programmed to interpolate the plurality of non-uniform images using the equation:

$$f'(x, y, z) = \sum_{k=-N}^{N} w(k) f(x, y, z+k);$$

where 'f (x,y,z) denotes the plurality of uniform images, f (x,y,z) denotes the plurality of non-uniform images, w denotes an interpolation coefficient, and N is a parameter that determines a size of the interpolation.

4. The CT system of claim 3 wherein the interpolation coefficient w is expressed as a Lagrange interpolator:

$$w(x_j) = \prod_{k=1, k \neq j}^{n} \frac{x - x_k}{x_j - x_k}.$$

5. The CT system of claim 1 wherein the computer is programmed to reduce noise in the plurality of non-uniform images prior to interpolating them to form the plurality of uniform images.

6. The CT system of claim 5 wherein the noise is reduced using one of adaptive filtering of projections followed by a filtered back-projection operation; adaptive post-processing on filtered back-projection generated images; and iterative reconstruction.

7. The CT system of claim 6 wherein the noise is reduced using an anisotropic diffusion process described by the equation:

$$\frac{\partial I(x, y, t)}{\partial t} = div[d(\|\nabla I\| \cdot \nabla I)];$$

where an intensity of pixel I(x,y) is updated based on a gradient of its value with its neighbor pixels, and d is a positive decreasing diffusion function.

8. The CT system of claim 1 wherein the controller is configured to energize the x-ray source while a contrast agent is passing through the subject.

9. The CT system of claim 8 wherein the contrast agent is iodine.

10. A method of perfusion map generation comprising:
transporting a patient table fore and aft along an axial dimension of a CT system to cover a z-length of a subject that is larger than a z-length of a CT detector of the CT system;
acquiring projection data over the z-length of the subject;
generating a plurality of temporally non-uniformly spaced subject images using the projection data;
applying an interpolation process to the plurality of temporally non-uniformly spaced subject images to form a plurality of interpolated images; and
applying a perfusion map generation process to the plurality of interpolated images to produce a final perfusion map.

11. The method of claim 10 wherein acquiring imaging data comprises dwelling the patient table at extremes of table motion and turning off an x-ray tube while the patient table dwells.

12. The method of claim 10 comprising injecting a contrast agent into the patient.

13. The method of claim 12 wherein the contrast agent includes iodine.

14. The method of claim 10 comprising applying a noise-reduction algorithm to the plurality of temporally non-uniformly spaced subject images prior to applying the interpolation process.

15. The method of claim 14 wherein the noise-reduction algorithm comprises one of adaptive filtering of projections followed by a filtered back-projection operation; adaptive post-processing on filtered back-projection generated images; and iterative reconstruction.

16. A non-transitory computer readable storage medium having stored thereon a computer program configured to:
obtain volume helical shuttle (VHS) data of a subject over a range of CT table motion, the range of CT table motion greater than a coverage of a CT detector;
generate a plurality of images using the VHS data;
interpolate the plurality of images to form a uniform grid having a finer temporal sampling increment than the obtained VHS data;
apply a perfusion map generation process to the uniform grid; and
present the perfusion map to a user.

17. The computer readable storage medium of claim 16 wherein the computer is programmed to interpolate the plurality of images using the equation:

$$f'(x, y, z) = \sum_{k=-N}^{N} w(k) f(x, y, z+k);$$

where f' (x,y,z) denotes the plurality of uniform images, f (x,y,z) denotes the plurality of non-uniform images, w denotes an interpolation coefficient, and N is a parameter that determines a size of the interpolation.

18. The computer readable storage medium of claim 17 wherein the interpolation coefficient w is expressed as a Lagrange interpolator:

$$w(x_j) = \prod_{k=1, k \neq j}^{n} \frac{x - x_k}{x_j - x_k}.$$

19. The computer readable storage medium of claim 16 wherein the computer is configured to suppress noise in the plurality of images prior to forming the uniform grid.

20. The computer readable storage medium of claim 19 wherein the computer is configured to suppress noise using an anisotropic diffusion process using an algorithm that includes the equation:

$$\frac{\partial I(x, y, t)}{\partial t} = div[d(\|\nabla I\| \cdot \nabla I)];$$

where an intensity of pixel I(x,y) is updated based on a gradient of its value with its neighbor pixels, and d is a positive decreasing diffusion function.

21. The computer readable storage medium of claim 16 wherein the computer is programmed to generate the plurality of images by recognizing a contrast agent within the subject.

22. The computer readable storage medium of claim 21 wherein the contrast agent is iodine.

* * * * *